US00PP11792P2

(12) United States Plant Patent
Heil

(10) Patent No.: US PP11,792 P2
(45) Date of Patent: Feb. 27, 2001

(54) CARNATION PLANT NAMED 'WHITE CAMPARI'

(75) Inventor: Jacob Johannes Heil, Aalsmeer (NL)

(73) Assignee: P. Kooij + Zonen B.V., Aalsmeer (NL)

( * ) Notice: Subject to any disclaimer, the term of this patent is extended or adjusted under 35 U.S.C. 154(b) by 0 days.

(21) Appl. No.: 09/379,264

(22) Filed: Aug. 23, 1999

(51) Int. Cl.[7] ..... A01H 5/00
(52) U.S. Cl. ..... Plt./274
(58) Field of Search ..... Plt./274, 279, 273, Plt./272

(56) References Cited

U.S. PATENT DOCUMENTS

P.P. 5,506 * 7/1985 van Andel ..... Plt./274

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Carnation plant named 'White Campari', characterized by its white-colored flowers; upright and mounded plant habit; good basal branching with about 10 lateral branches developing after pinching; dark green leaves; rapid growth rate; fragrant flowers; and good postproduction longevity.

1 Drawing Sheet

BACKGROUND OF THE INVENTION

The present invention relates to a new and distinct cultivar of Carnation plant, botanically known as *Dianthus caryophyllus*, and hereinafter referred to by the cultivar name White Campari.

The new Carnation was discovered by the Inventor in a controlled environment in Aalsmeer, The Netherlands, in 1998, as a naturally-occurring mutation of *Dianthus caryophyllus* 'Campari' (U.S. Plant Patent application Ser. No. 09/379,266). The new Carnation was observed as a single plant in a group of flowering plants of the parent cultivar. The selection of this plant was based on its unique flower color.

Asexual reproduction of the new cultivar by terminal cuttings taken at Aalsmeer, The Netherlands, has shown that the unique features of this new Carnation are stable and reproduced true to type in successive generations of asexual reproduction.

SUMMARY OF THE INVENTION

The following traits have been repeatedly observed and are determined to be the unique characteristics of 'White Campari'. These characteristics in combination distinguish 'White Campari' as a new and distinct cultivar:

1. White-colored flowers.
2. Upright and mounded plant habit.
3. Good basal branching with about 10 lateral branches developing after pinching.
4. Dark green leaves.
5. Rapid growth rate.
6. Fragrant flowers.
7. Good postproduction longevity.

Plants of the new Carnation are similar to plants of the parent cultivar, 'Campari', in most horticultural characteristics, however significantly differ in flower color as plants of the cultivar 'Campari' have red-colored flowers.

BRIEF DESCRIPTION OF THE PHOTOGRAPH

The accompanying colored photograph illustrates the overall appearance of the new cultivar, showing the colors as true as it is reasonably possible to obtain in colored reproduction of this type. The photograph comprises a side perspective view of typical plants of 'White Campari'. Flower and foliage colors in the photograph may appear different from the actual colors due to light reflectance.

DETAILED BOTANICAL DESCRIPTION

The cultivar White Campari has not been observed under all possible environmental conditions. The phenotype may vary somewhat with variations in environment such as temperature and light intensity, without, however, any variance in genotype. The following observations, measurements and comparisons describe plants grown 9-cm pots in Aalsmeer, The Netherlands, under conditions approximating commercial practice in a glass-covered greenhouse with day and night temperatures averaging about 20 and 14° C., respectively. Plants were about 10 weeks old after planting.

In the following description, color references are made to The Royal Horticultural Society Colour Chart except where general terms of ordinary dictionary significance are used.

Botanical classification: *Dianthus caryophyllus* cultivar White Campari.

Parentage: Naturally-occurring mutation of *Dianthus caryophyllus* 'Campari', U.S. Plant Patent application Ser. No. 09/379,266.

Propagation:

*Type cutting.*—Terminal cuttings.

*Time to initiate roots.*—About 5 days during the summer and about 7 days during the winter.

*Time to develop roots.*—About 20 days during the summer and about 28 days during the winter.

*Root description.*—Fine, freely branching.

Plant description:

*Plant form.*—Upright and mounded; inverted triangle.

*Growth and branching habit.*—Good branching with about ten lateral branches developing after pinching, dense and bushy growth. Appropriate for 9-cm and larger containers.

*Vigor.*—Vigorous.

*Growth rate.*—Rapid growth rate; starting with a plant grown in a 5-cm container, about 10 weeks are required to produce a flowering plant in a 15-cm container.

*Plant height.*—About 15 cm.

*Plant width.*—About 15 cm.

*Lateral branches.*—Diameter: About 1.5 mm. Internode length: About 2 cm. Color: 133B.

*Foliage description.*—Leaves simple; symmetrical; abundant; opposite; sessile. Quantity of leaves per lateral branch: About 26. Length: About 5cm. Width: About 4.5 mm. Shape: Linear; apex, acute; base, cordate; margin, entire. Texture: Smooth, glabrous; waxy. Color: Young foliage, upper surface: 136B. Young foliage, lower surface: 139B. Fully expanded foliage, upper surface: 136B. Fully expanded foliage, lower surface: 136B. Venation, upper surface: 136B. Venation, lower surface: 138A.

Flower description:

*Flower type and habit.*—White-colored double flowers. Freely and continuously flowering. Usually about two or three flowers per lateral branch; typically about 10 open flowers per plant. Flowers flat and convex. Flower positioned mostly above the foliage; typically facing upright or outward. Flowers persistent.

*Flowering season.*—Year-round under greenhouse conditions. In the garden, flowering is continuous during the summer.

*Flower longevity.*—About two weeks, on the plant.

*Fragrance.*—Moderately strong, clove-like fragrance typical of the species.

*Flower size.*—Diameter: About 3 cm. Depth: About 3 cm.

*Flower buds.*—Length: About 1.3 cm. Diameter: About 8 mm. Shape: Ovate. Color: 143B. Rate of opening: About one week.

*Petals/petaloids.*—Quantity: About 25, overlapping. Length: About 3 cm. Width: About 1.5 cm. Shape: Mostly rounded; apex and base, acute; margin, serrated. Texture: Rippled. Color: When opening and fully opened, upper surface: White, 155C. When opening and fully opened, lower surface: White, 155C.

*Sepals.*—Quantity: Five. Calyx length: About 2 cm. Calyx width: About 1 cm. Shape: Triangular; apex, rounded; margin, entire. Texture: Smooth. Color: Upper surface: 144C. Lower surface: 144A.

*Peduncles.*—Length: About 2 mm. Angle: Erect. Strength: Strong. Color: 144A.

*Reproductive organs.*—Androecium: Stamen number: Up to five. Anther length: About 1 mm. Anther shape: Oblong. Anther color: 39D. Amount of pollen: Scarce. Gynoecium: Pistil number: Two. Pistil length: About 2 cm. Style length: About 2 cm. Style color: 4D. Stigma color: 39D. Ovary color: 144C.

*Seed.*—Seed development has not been observed.

Disease resistance: Under commercial conditions, resistance to pathogens common to Dianthus has not been observed.

It is claimed:

1. A new and distinct cultivar of Carnation plant named 'White Campari', as illustrated and described.

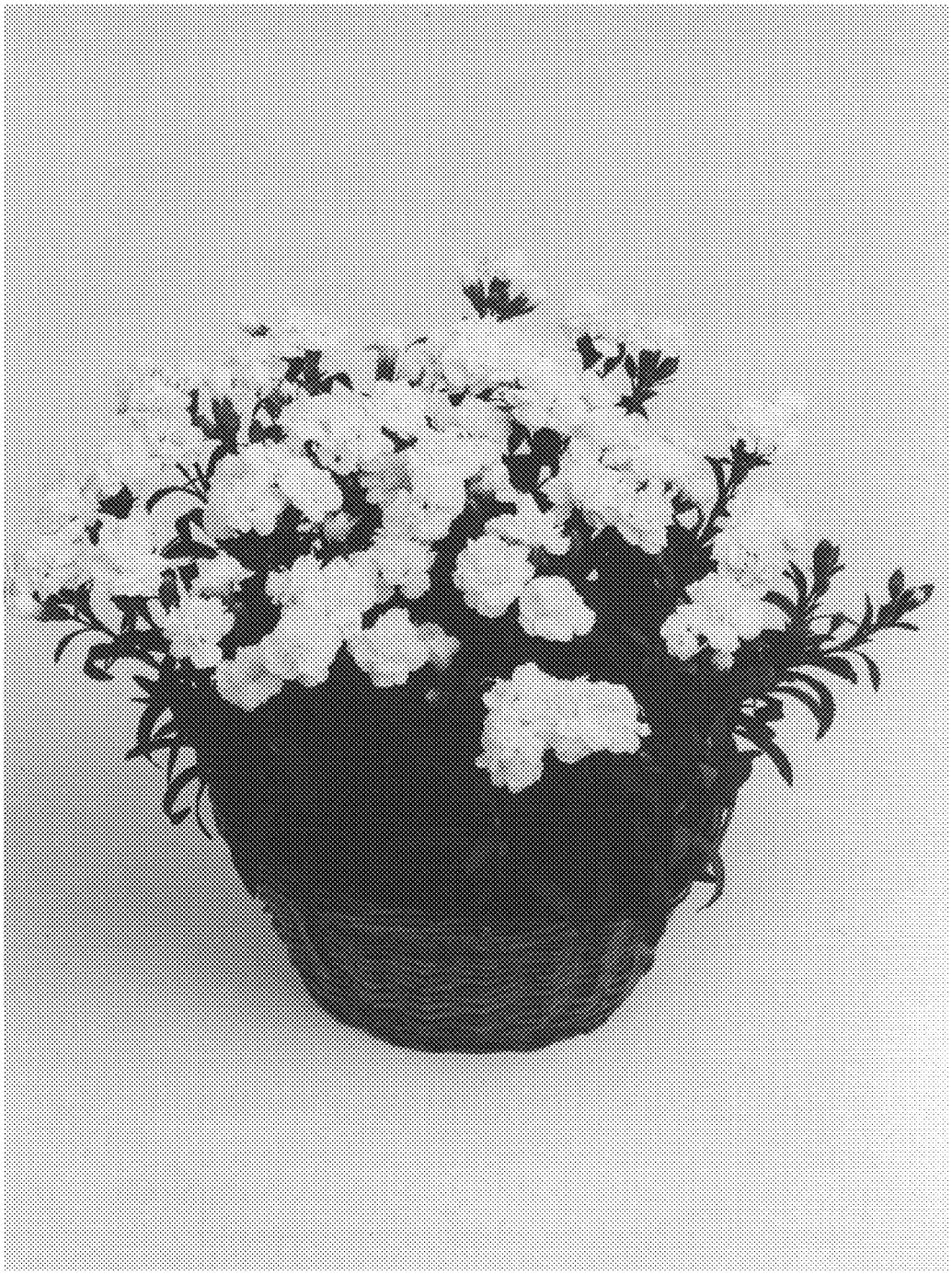

* * * * *